United States Patent [19]
Costanzo et al.

[11] Patent Number: 5,998,219
[45] Date of Patent: Dec. 7, 1999

[54] SAMPLE COLLECTING METHOD AND APPARATUS

[75] Inventors: Stephen Costanzo; Richard Baritot, both of Rochester, N.Y.

[73] Assignee: Bausch & Lomb Incorporated, Rochester, N.Y.

[21] Appl. No.: 09/061,640

[22] Filed: Apr. 16, 1998

[51] Int. Cl.⁶ ..................................................... G01N 1/10
[52] U.S. Cl. ...................... 436/180; 435/30; 73/864.11; 73/864.14; 73/864.34
[58] Field of Search ........................... 73/864.11, 864.14, 73/864.34; 436/178, 180; 435/30

[56] References Cited

U.S. PATENT DOCUMENTS 4,025,306  5/1977  Studer .
4,829,005  5/1989  Friedman et al. ...................... 436/296

*Primary Examiner*—David A. Redding
*Attorney, Agent, or Firm*—Mary Anne Magee; Chris P. Konkol

[57] ABSTRACT

The present invention is directed to methods and apparatus for collecting and pooling the contents of a multiple number of individual sample containers, the apparatus comprising an autoclavable collection bottle capped with a closure-adaptor means having at least one passageway for transfering the fluid contents of the sample containers into the collection bottle. In one embodiment of the invention, the closure-adaptor means comprises a plastic retainer ring for securely holding a flanged cylindrical stopper in which the above-mentioned passageway is formed. Still another aspect of the invention relates to a method of sample testing comprising collecting a pooled sample of a solution or gel, inoculating and/or filtering the pooled sample, and analyzing the inoculated sample or the filter retentate for microbial contamination. For instance, the present method may be used for carrying out either filtered membrane sterility testing or direct transfer preservative efficacy testing of a health care or pharmaceutical product.

13 Claims, 3 Drawing Sheets

SAMPLE COLLECTING METHOD AND APPARATUS

BACKGROUND OF THE INVENTION

1. Field of the Invention

This invention relates in general to methods and apparatus for collecting and testing a viscous liquid or gel. Apparatus and methods are disclosed for collecting and pooling the contents of a plurality of relatively small containers. The invention is especially useful for microbiological testing a product sample with respect to sterility, bacteriostasis, or preservative effectiveness.

2. Description of the Related Art

In the production of consumer products in the health care or pharmaceutical industries, in which liquids of various viscosities are sold in relatively small containers for individual use, microbiological testing on a statistical basis may be required to ensure that the products are substantially free of microorganisms such as bacteria, fungi and molds. Recognized procedures for such microbiological testing may involve the direct transfer method or the membrane filter method. These methods are described in the United States Pharmacopeia (USP) 23 (1994), U.S. Food and Drug Administration Guidelines (FDA), and the Japanese Pharmacopeia XII suppl. II, all incorporated herein by reference.

One conventional method of microbiological testing is the antimicrobial preservative-effectiveness procedure (or "preservative efficacy" procedure), normally a direct transfer method. In the direct transfer method, microorganisms are inoculated directly into a sample solution, provided that the sample size of that solution is of sufficiently ample size (normally at least 20 mL). The solutions are then plated out in conventional media and subsequently examined at periodic intervals of 7, 14, 21 and 28 days. When the amount of sample obtained from a single product container is too small to allow the sample to be directly inoculated, a plurality of containers from a sample lot may be pooled together (under sterile conditions to avoid contamination) and then the pooled contents directly inoculated.

Another standard microbiological test, sterility testing, typically involves the membrane filter method. In the membrane filter method, a test sample is filtered through a membrane filter. Typically, the filter is then rinsed to remove any microbiocides, after which the filter holding the retentate from the test sample, or a preselected fraction of this filter, is incubated in a suitable medium. Optionally, the medium may be added onto the membrane filter while remaining in the filtration device.

In the health care industry, in order to obtain an adequate amount of test solution for sterility testing a product, twenty bottles or more per sample lot may need to be pooled or combined. In order to obtain an adequate amount of test solution for the previously mentioned preservative efficacy test, as many as eighty containers or bottles per sample lot may need to be combined. The pooling of such large numbers of bottles can be very time consuming and difficult when the sample containers are small, the contents are relatively viscous, and/or the bottle is designed to expel the liquid contents dropwise. If the containers have a separate top piece or dispenser tip that is removable from the container, then the tip can be removed, the bottle inverted, and the solution dispensed relatively easily, especially when the solution is non-viscous. Typically, however, the dispensing tip snuggly fits into the neck portion of a bottle, and removal of such container tips can be time consuming and laborious.

It may be particularly problematic or difficult to transfer a viscous solution from a single-piece container having a dispensing tip that is an irremovable or integral part of the container holding the solution. Such containers include form-filled bottles or tubes, either unit-dose or multi-dose containers. A conventional method of collecting a sample from a container having an irremovable tip involves repetitively squeezing the outside surface of the container to force its contents out its dispensing orifice as quickly as possible. To dispense the entire contents of the necessary number of bottles by such a method may be a strenuous and monotonous task, particularly when the bottles are semi-rigid and designed to deliver droplets. Also, such a method may result in sample contamination as a result of air being drawn back into a container.

There are many devices available for sterility testing of liquids. For instance, U.S. Pat. No. 4,036,698 relates in general to the testing of pharmacological products. The patent describes and claims an apparatus designed to carry out a membrane filtration method wherein the solution to be tested is added to a filter apparatus comprising a cylindrical canister having two ports at one end and a single port at the opposite end. One of the two ports at the one end is provided with a hydrophobic microporous filter that allows the flow of air therethrough in either direction while screening out any microorganisms. A second membrane filter is positioned within the cylinder such that test solution passes therethrough, trapping bacteria or fungi on the membrane filter. This apparatus does not solve or address the above-mentioned difficulties of collecting a sufficient amount of sample contents from many relatively small containers, particularly containers designed for the delivery of droplets.

In view of the above, there is a need for a more efficient method and apparatus for collecting samples for the microbiological testing of products produced in the pharmaceutical or health care industries. There is a need for a more efficient method of collecting samples from product containers designed to deliver droplets during individual use.

SUMMARY OF THE INVENTION

The present invention is directed to methods and apparatus for collecting samples of solutions or gels from a plurality of product containers. The present apparatus comprises an autoclavable collection bottle enclosing a collection chamber and a unique closure-adaptor means for capping the bottle. The closure-adaptor means has a first passageway communicating at one end with the collection chamber and adapted, at its opposite end, for attachment to a sample container. The first passageway comprises a means for receiving and securely holding the uncapped top portion of the sample container such that the liquid or gel contents of the sample container can be dispensed through the passageway and into the collection chamber of the bottle.

A second passageway, in either the collection bottle or the closure-adapter means, is adapted for attaching to a flexible conduit or hose in communication with a vacuum source in order to create a vacuum in the collection chamber and to draw the internal contents of the sample container through the first passageway and into the collection chamber.

Another aspect of the present invention is directed to a method of collecting a fluid, including viscous liquids or gels, from a multiple number of fluid-holding containers, which method comprises the steps of (1) securely attaching the top portion of a fluid-holding sample container to a first passageway in a closure-adaptor means that is sealingly attached to the top of a collection bottle, and (2) applying a vacuum through a second passageway, in the bottle or in the closure-adaptor means attached to the container, for pulling at least a portion of the fluid contents of the sample container into the collection bottle. Steps (1) and (2) above are repeated with a preselected number of sample containers by consecutively attaching a container to the collection bottle while under vacuum, drawing the fluid contents of the sample container into the collection chamber of the bottle, and unattaching the empty or depleted sample container from the closure-adaptor means before attaching the next sample container.

In still another aspect of the invention, a method of sample testing comprises (1) collecting a pooled sample of a solution or gel, as above described, (2) inoculating and/or filtering the pooled sample, and (3) analyzing the inoculated sample or the filter retentate for microbial contamination. For instance, the present method may be used for carrying out either direct or filtered-membrane sterility testing, preservative efficacy testing or biostasis testing. By way of example, the invention is useful for the microbiological testing of health care products such as ophthalmic eye drops, dry eye ointments, or contact-lens care solutions.

In one particular embodiment of the invention, the closure-adaptor means for attachment to a collection bottle comprises a stopper means that is secured in place by a retainer ring having a circular opening adapted to coaxially fit about the stopper means and having internal threads for screwing onto the top of the collection bottle. The stopper means comprises a generally cylindrical top portion around the bottom perimeter of which is a circular flange such that the bottom surface of the circular flange is sealingly pressed against the top rim of the collection bottle by means of the inside top surface of the retainer ring when screwed onto the collection bottle, the cylindrical portion of the stopper means thereby projecting upward through the circular opening of the retainer ring.

DESCRIPTION OF PREFERRED EMBODIMENTS

Figure 1:
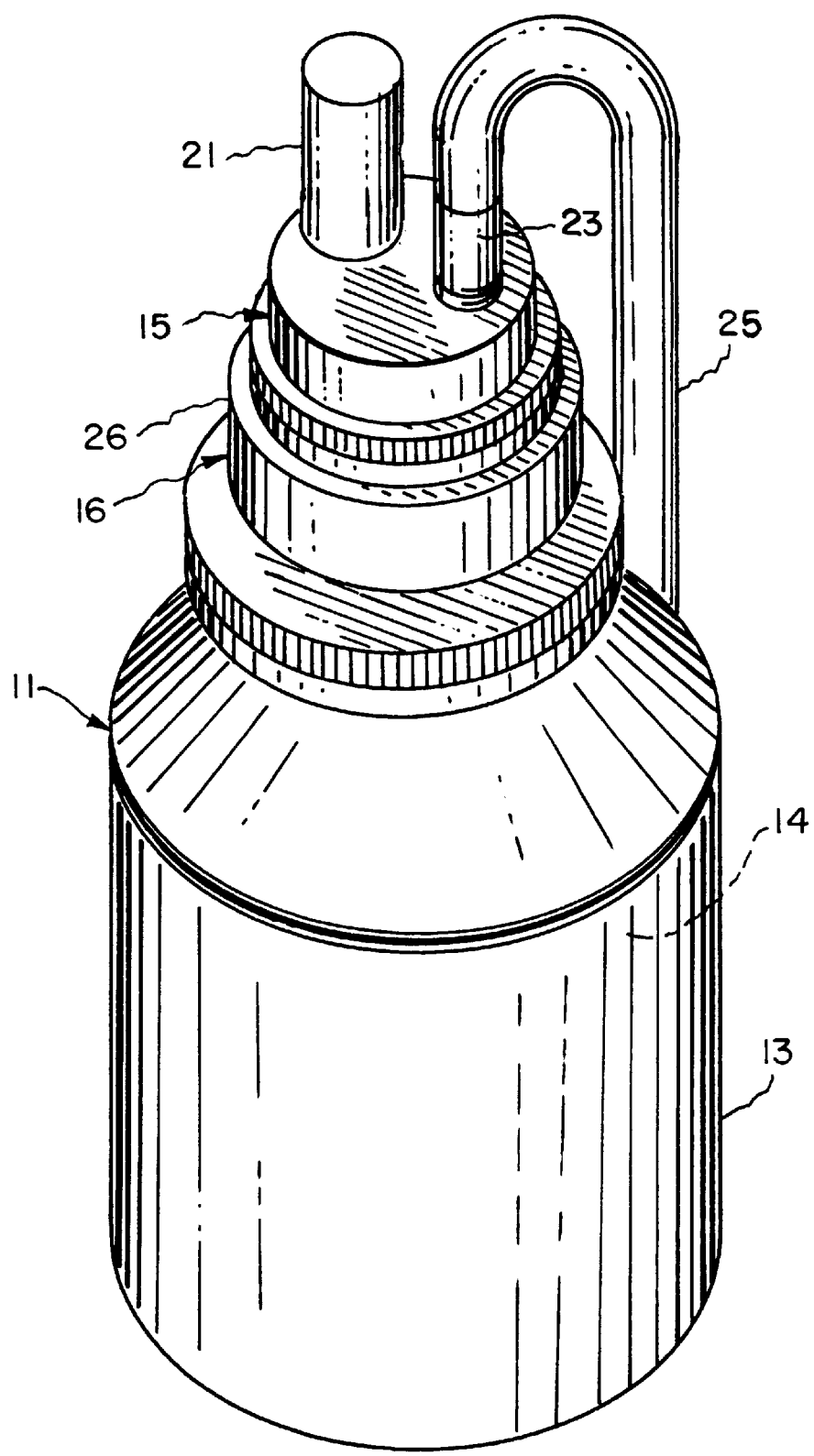
FIG. 1 is an perspective view of the a collection apparatus constructed in accordance with the principles of this invention.

As mentioned above, the present invention relates to methods and apparatus for collecting and testing a relatively viscous liquid or gel that is contained in a plurality of relatively small containers. The invention is particularly applicable to microbiological testing such as sterility, bacteriostasis, and/or preservative effectiveness testing.

The present apparatus comprises an autoclavable collection bottle enclosing a collection chamber and an autoclavable closure-adaptor means for closing the collection bottle while collecting a sample. The apparatus has at least two passageways each in open communication at one end with the collection chamber. A first passageway comprises a means for receiving and attaching the uncapped top portion of a sample container such that the liquid or gel contents of the container can be dispensed through the first passageway and into the collection chamber of the bottle. A second passageway is adapted for communication with a vacuum source preferably via a flexible conduit or hose.

The closure-adaptor means may be integrally molded from a suitable plastic material able to withstand the temperatures used during autoclaving. In a preferred embodiment, the closure-adaptor means is an assembly comprising a plastic retainer ring internally threaded for attachment to the externally threaded neck portion of a transparent collection bottle, the top of the retainer ring having a circular opening for securely holding a flanged substantially cylindrical stopper in which the above-mentioned first and second passageways are formed. As indicated above, the first passageway provides a means of transferring the internal contents of a sample container that is securely and sealingly attached to one end of the passageway into the internal space or chamber of the collection bottle which is in communication with the opposite end of the passageway. Accordingly, the first passageway in the closure-adpator means may be internally threaded for attaching a complementarily externally threaded top portion of the sample container.

Alternate means of attaching a sample container to the closure adaptor means may be employed. For example, a compression fitting may be used to attach a sample container to a passageway in the closure-adapter means. Various compression fitting mechanisms are known to those skilled in the art. For example, the top of the closure-adaptor means may comprise a cylindrical tubular projection having an externally threaded top portion to which attaches an internally threaded retaining ring having a circular opening adapted for receiving the top end of a sample container. To provide a compression fitting, a deformable plastic sealing ring with a circular opening aligned with the circular opening in the retaining ring is placed in the internal space between the upper inside (ring-shaped) surface of the retaining ring and an internal (ring-shaped) ledge inside the cylindrical tubular projection. When the end of the sample container is inserted in series through the circular opening of the retaining ring and through the circular opening of the sealing ring, and the retaining ring is screwed onto the end of the cylindrical tubular projection, the sealing ring is made to sealingly and fixedly engage the dispensing end of the sample container. The compression of the sealing ring, between the inside surfaces of the retaining ring and the internal ledge of the tubular projection, decreases the diameter of the circular opening in the sealing ring. A compression ring, made of a metal or rigid plastic material, may be alignedly placed adjacent and below the sealing ring, which compression ring is axially downsloping or conical in shape. Such a compression ring is designed to more effectively decrease the circular opening of the sealing ring during compression. One advantage of such a compression fitting for securing a sample container to the closure-adpator means is that, by means of substituting different sealing rings each having a circular opening with a different internal diameter, the closure-adapator means may be employed with respect to variously sized sample containers.

As indicated above, a second passageway supplies a vacuum for drawing or pulling at least a portion of the internal contents of the sample container into the collection chamber. The second passageway is, therefore, preferably adapted for direct or indirect connection to a flexible conduit or hose attached at its distal end to a suitable vacuum source. The proximate end of the flexible conduit may be attached to the closure-adaptor means by any conventional connection means. For instance, the second passageway in the closure-adaptor means may also be internally threaded at one end of the passageway to receive the proximate externally threaded end of a rigid tubular connecting piece. The distal end of the rigid tubular piece, which may be unthreaded, may be attached to the proximate end of the flexible conduit whereby the flexible conduit forms a sleeve-like segment over the distal end of the rigid tubular piece.

Alternatively, the second passageway may extend through the side of the collection bottle. For example, a vacuum hose may be connected to a tubular projection extending perpendicularly from the side of the collection bottle. The position of the tubular projection, which may depend on the size and shape of the container, should be designed so that when a vacuum is provided to the bottle, the suction of the vacuum entering the bottle does not cause the sample solution to be drawn from the sample container into the tubular projection or diverted onto the side walls of the bottle. Preferably, in operation, a stream of the sample solution entering the collection chamber through the first passageway should fall in a substantially uninterrupted line to the a pool at bottom of the chamber.

With reference now to the drawings, FIG. 1 illustrates in perspective a preferred embodiment of an apparatus for collecting fluid. The apparatus, generally indicated at 11, comprises a collection bottle 13 defining a collection chamber 14. A closure-adaptor means 16, comprising a retaining ring 26 for holding in place a stopper means 15, is connected to a fluid container 21 for sampling purposes. The fluid container 21 is relatively small in size and may contain a few milliliters of a viscous fluid. In the embodiment shown in FIG. 1, the fluid container is designed to hold a contact lens care solution, in particular a liquid enzyme product. However, the present invention is obviously applicable to collecting the contents of containers holding a variety of healthcare or pharmaceutical products, including, but not limited to, ophthalmic eye drops or ointments.

The stopper means 15 is connected to a rigid tubular piece 23 that in turn is connected to a flexible rubber hose 25 for communication with any suitable vacuum source (not shown). Sufficient vacuum is necessary to pull the fluid from fluid container 21 into collection chamber 14 of the collection bottle 13.

Figure 2:
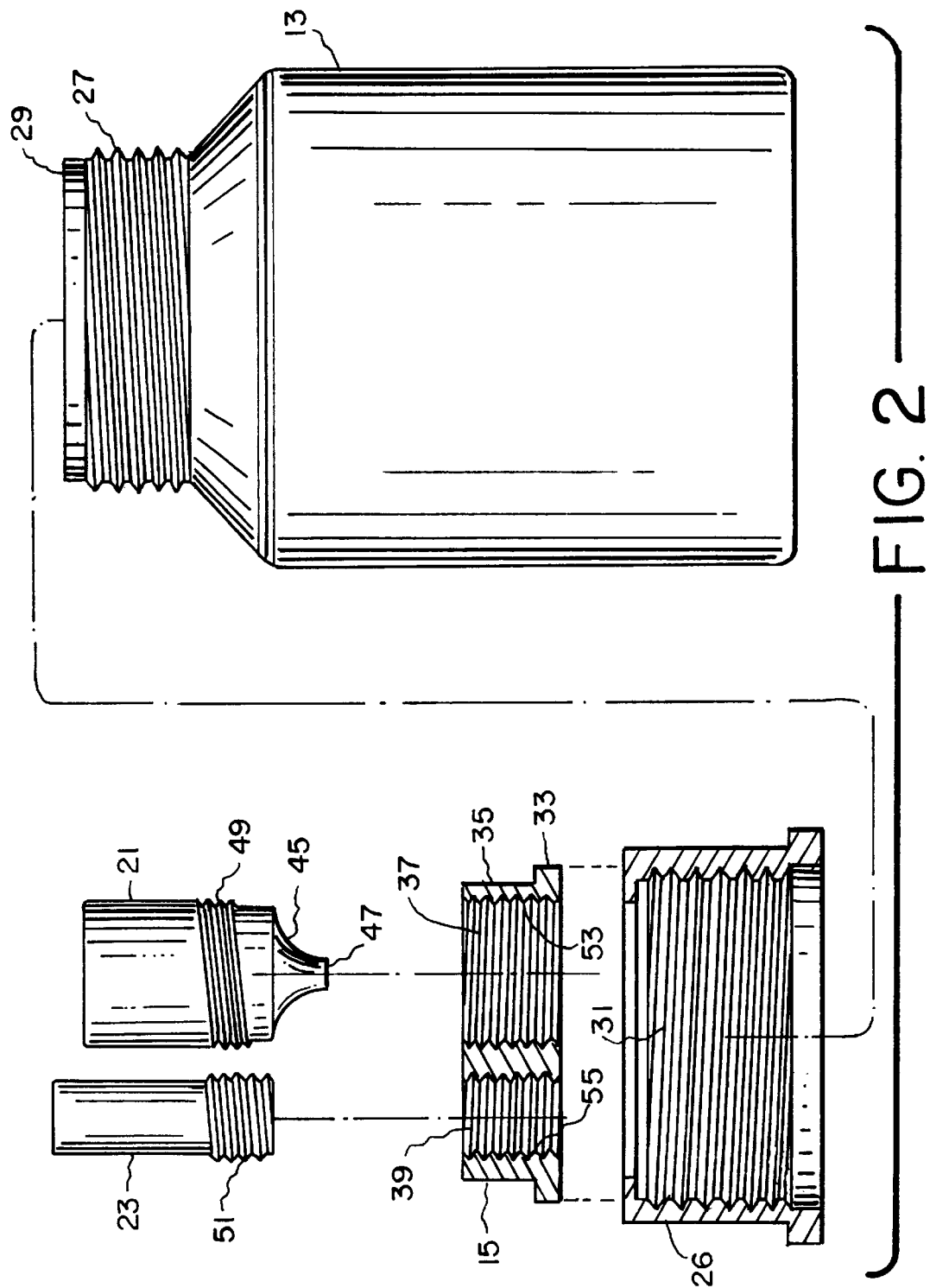
FIG. 2 is an exploded view of a preferred embodiment of a collection apparatus in use according to the present invention comprising a collection bottle, a sample container, and in cross-sectional view, a retainer ring and a stopper means.

FIG. 2 shows an exploded view of the apparatus of FIG. 1. A collection bottle 13 comprises external threads 27 extending over a neck portion of the bottle up to a rim 29. The collection bottle is preferably made from a transparent, autoclavable material such as glass or plastic. A retainer ring 26 has internal threads 31 for mating with the external threads 27 of the collection bottle. The external surface of the retainer ring may be fluted (scalloped from a cross-sectional top view) in order to facilitate gripping, tightening or screwing the retainer ring over the rim and onto the external threads at the top of the collection bottle. A stopper means 15, adapted to be held in place by the retainer ring 26, comprises a flange 33 and a generally cylindrically shaped upper portion 35. The stopper means 15, in the present embodiment, has two threaded passageways, a first passageway 37 and a second passageway 39.

Figure 3:
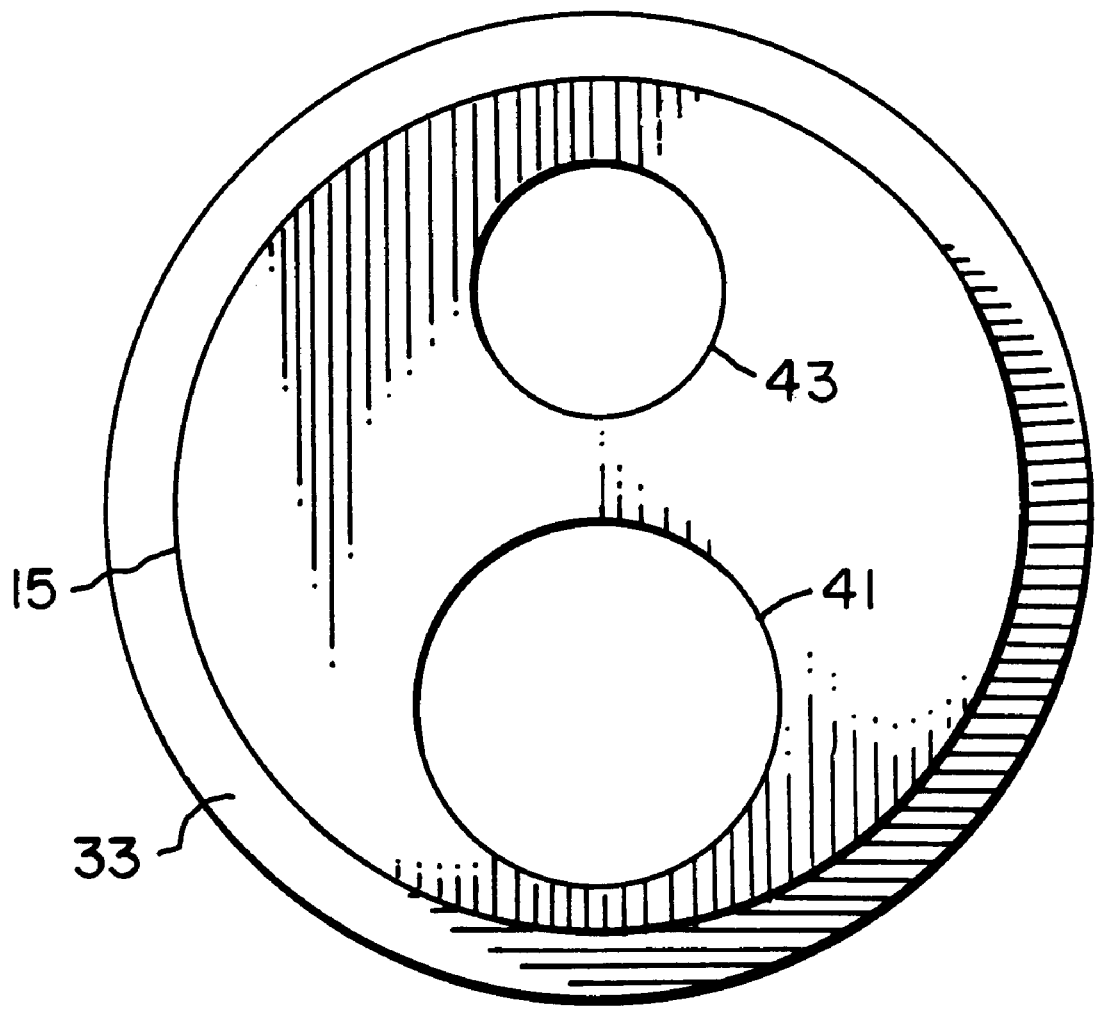
FIG. 3 is a top view of the stopper means according to the embodiment of FIG. 2.

Referring now to FIG. 3, a top view of the stopper means 15 shows the circular perimeter of the flange 33 and the respective openings or ports 41 and 43, respectively, of the first and second passageways 37 and 39. The stopper means is preferably made of stainless steel in which the passageways can be conventionally tooled.

Returning to FIG. 2, the passageway 37 is adapted to receive a fluid container 21 comprising dispensing end 45, orifice 47 and external threads 49 complementary to internal threads 53 of passageway 37. The second passageway 39 is adapted to receive a tubular connector piece 23 having external threads 51 complementary to internal threads 55 of passageway 39.

The embodiment of FIGS. 1 to 3 has the advantage that various stopper means designed for sampling differently shaped or sized sample containers may be assembled with the same standard collection bottles and retainer rings. Alternatively, an integral single-piece closure-adapter means may be custom designed and molded from a suitable plastic material for specific use with a specific product container.

In operation of the apparatus shown in FIGS. 1 to 3, an uncapped fluid-holding sample container is sealingly attached to one end of the first passageway in the closure-adaptor means that in turn is sealingly attached to the top of the collection bottle. The other end of the first passageway is in open communication with the collection chamber of the collection bottle. As indicated above, the sample container is attached to the one end of the first passageway by screwing the externally threaded top portion of the sample container into the internally threaded end of the first passageway. A sufficient vacuum is then applied through the second passageway in the closure-adaptor means in order to pull at least a portion of the fluid contents of the sample container into the collection bottle. A suitable vacuum ranges from 24 to 30 inches Hg, preferably 25 to 29 inches Hg. After drawing out at least a portion of the fluid contents of the sample container, preferably the entire contents of the sample container, into the collection chamber, the empty or depleted sample container is unscrewed and detached from the first passageway. The procedure is repeated with a plurality of sample containers until the desired amount of the fluid, either a gel or solution, is collected for testing or analysis.

For use in collecting a pooled sample for microbiological testing, the apparatus used must first be free of microorganisms. Several conventional methods known to those skilled in the art that can be employed to sterilize the apparatus. Preferably, the apparatus is sterilized by means of a laboratory autoclave.

In one method according to the present invention, a pooled sample is collected from a plurality of sample containers, and then the pooled sample is inoculated with a test microbial agent for testing the preservative efficacy of the fluid contained in the sample containers. In another embodiment, the pooled sample may be poured over the filter of a standard filter device used for microbiological testing and a vacuum used to draw the sample solution through the filter. The collected retentate or residue is then placed in a medium and, after incubation, its sterility tested according to standard procedures.

The apparatus must be sterilized, preferably autoclaved, for reuse. The closure-adapter means, including the stainless steel stopper means and the retainer ring, may be separately sterilized and packaged until reassembled with the collection bottle for reuse.

The invention is especially advantageous for removing a viscous liquid or gel from a product container through an orifice in the dispensing tip of the container. The invention is applicable to products having a viscosity of zero to 5000 cps. Solutions typically have viscosities of zero to 1500 cps, although gels may have higher viscosities. Typically, the sample containers contain 1 to 60 mL of liquid or gel, often less than 30 mL of liquid.

When the product being sampled is from containers adapted to deliver droplets of the product, the top of the container typically has a pointed tip with a small orifice. Such orifices typically are 10 micron to 150 micron in diameter, more typically 30 micron to 75 micron in diameter.

As mentioned above, the present invention can be used to collect and test a variety of products, including prescription or non-prescription pharmaceutical products, ophthalmic or other health care products, and food products. The products may be in the form of a gel or solution. The invention is especially applicable to collecting samples of products that are relatively viscous solutions or gels intended for dropwise delivery during consumer use.

We claim:

1. A method of collecting and pooling the fluid contents of a plurality of relatively small sample containers into a relatively larger collection bottle, which method comprises the following steps:

(a) sealingly attaching an uncapped fluid-holding sample container to one end of a first passageway in a closure-adaptor means that is sealingly attached to the top of the collection bottle, the other end of the first passageway being in communication with the inside of the collection bottle, (b) applying a vacuum through a second passageway in communication with the inside of the container for pulling at least a portion of the fluid contents of the sample container into the collection bottle, and (c) unattaching the empty or depleted sample container from the first passageway, (d) repeating steps (a) to (c) with a plurality of sample containers until a predetermined amount of fluid, either a gel or solution, has been collected in the collection bottle.

2. The method of claim 1, wherein the sample container is attached to one end of the first passageway by means of external threads at the top of the sample container which threads are complementary to the internal threads in the first passageway.

3. The method of claim 1, wherein the vacuum may be provided through a flexible conduit attached via a connector means to a second passageway in the closure-adpator means.

4. The method of claim 1, wherein the sample container is fixedly and securely attached to one end of the first passageway by means of a deformable sealing ring in a compression fitting.

5. The method of claim 1, wherein the second passageway extends through the closure-adaptor means.

6. The method of claim 1, wherein the second passageway extends through a side wall of the collection bottle.

7. The method of claim 1, wherein the fluid has a viscosity ranging from 0 to 1500 cps.

8. The apparatus of claim 7, wherein the sample container initially contains less than 30 mL of liquid.

9. The method of claim 1, wherein the sample container is adapted to deliver droplets of product during use.

10. The method of claim 9, wherein the top of the sample container has a pointed lip terminating in an orifice designed for dropwise delivery of the product during use.

11. The method of claim 1, wherein the gel or solution is a prescription or non-prescription pharmaceutical product.

12. The method of claim 11, wherein the gel or solution is an ophthalmic product intended to be instilled onto an eye.

13. The method of claim 1, wherein the fluid is a solution that is intended to be added dropwise into a larger amount of another solution.

* * * * *